(12) United States Patent
Partanen et al.

(10) Patent No.: US 12,396,653 B2
(45) Date of Patent: *Aug. 26, 2025

(54) MRI-BASED FEEDBACK CONTROL OF ULTRASOUND BASED MECHANICAL FRACTIONATION OF BIOLOGICAL TISSUE

(71) Applicants: University of Washington, Seattle, WA (US); Koninlkijke Philips N.V., AE Eindhoven (NL)

(72) Inventors: Ari Ilkka Mikael Partanen, Andover, MA (US); Wayne Kreider, Seattle, WA (US); Vera Khokhlova, Seattle, WA (US)

(73) Assignees: University of Washington, Seattle, WA (US); Koninlkijke Philips N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 17/543,276

(22) Filed: Dec. 6, 2021

(65) Prior Publication Data

US 2022/0304588 A1     Sep. 29, 2022

Related U.S. Application Data

(63) Continuation of application No. 15/737,670, filed as application No. PCT/US2016/038052 on Jun. 17, 2016, now Pat. No. 11,224,356.

(Continued)

(51) Int. Cl.
*A61B 5/055*     (2006.01)
*A61B 5/00*      (2006.01)
(Continued)

(52) U.S. Cl.
CPC ............ *A61B 5/055* (2013.01); *A61B 5/0035* (2013.01); *A61B 5/01* (2013.01); *A61B 5/02* (2013.01);
(Continued)

(58) Field of Classification Search
CPC ... A61B 5/0035; A61B 5/01; A61B 2090/374; A61N 7/02
See application file for complete search history.

(56) References Cited

U.S. PATENT DOCUMENTS 5,485,839 A   1/1996  Aida et al.
5,762,066 A   6/1998  Law et al.
(Continued)

FOREIGN PATENT DOCUMENTS

WO   2013153506 A1   10/2013
WO   2015148938      10/2015

OTHER PUBLICATIONS

Canney, et al., "Shock-induced heating and millisecond boiling in gels and tissue due to high intensity focused ultrasound," Ultrasound Med. Biol., vol. 36, No. 2, pp. 250-267, 2010.

(Continued)

*Primary Examiner* — Amelie R Davis
(74) *Attorney, Agent, or Firm* — McDonnell Boehnen Hulbert & Berghoff LLP

(57) ABSTRACT

Disclosed herein are example embodiments of devices, systems, and methods for mechanical fractionation of biological tissue using magnetic resonance imaging (MRI) feedback control. The examples may involve displaying an image representing first MRI data corresponding to biological tissue, and receiving input identifying one or more target regions of the biological tissue to be mechanically fractionated via exposure to first ultrasound waves. The examples may further involve applying the first ultrasound waves and, contemporaneous to or after applying the first ultrasound waves, acquiring second MRI data corresponding to the biological tissue. The examples may also involve determining, based on the second MRI data, one or more second parameters for applying second ultrasound waves to the (Continued)

biological tissue, and applying the second ultrasound waves to the biological tissue according to the one or more second parameters.

16 Claims, 14 Drawing Sheets

Related U.S. Application Data

(60) Provisional application No. 62/181,448, filed on Jun. 18, 2015.

(51) Int. Cl.
| | |
|---|---|
| A61B 5/01 | (2006.01) |
| A61B 5/02 | (2006.01) |
| A61B 90/00 | (2016.01) |
| A61N 7/00 | (2006.01) |
| A61N 7/02 | (2006.01) |
| G01R 33/48 | (2006.01) |
| G01R 33/50 | (2006.01) |
| G01R 33/56 | (2006.01) |
| G01R 33/563 | (2006.01) |

(52) U.S. Cl.
CPC ........... *A61N 7/02* (2013.01); *G01R 33/4814* (2013.01); *G01R 33/50* (2013.01); *G01R 33/5602* (2013.01); *G01R 33/56341* (2013.01); *G01R 33/56358* (2013.01); *A61B 2090/374* (2016.02); *A61N 2007/006* (2013.01)

(56) References Cited

U.S. PATENT DOCUMENTS

| | | | |
|---|---|---|---|
| 6,501,978 | B2 | 12/2002 | Wagshul et al. |
| 6,516,211 | B1 | 2/2003 | Acker et al. |
| 6,542,767 | B1 | 4/2003 | McNichols et al. |
| 7,246,939 | B1 | 7/2007 | Gultekin |
| 2003/0233045 | A1 | 12/2003 | Vaezy et al. |
| 2004/0242999 | A1 | 12/2004 | Vitek et al. |
| 2006/0122509 | A1 | 6/2006 | Desilets |
| 2008/0146912 | A1 | 6/2008 | Richard |
| 2008/0221649 | A1 | 9/2008 | Echague et al. |
| 2009/0143676 | A1 | 6/2009 | Matsumura |
| 2010/0094178 | A1 | 4/2010 | Lacoste |
| 2010/0125192 | A1 | 5/2010 | Chopra et al. |
| 2010/0179414 | A1* | 7/2010 | Kuhn .................. A61N 7/02 382/107 |
| 2010/0191157 | A1 | 7/2010 | Sanghvi |
| 2010/0210976 | A1 | 8/2010 | Darlington et al. |
| 2010/0228122 | A1 | 9/2010 | Keenan et al. |
| 2011/0054315 | A1 | 3/2011 | Roberts et al. |
| 2011/0251528 | A1* | 10/2011 | Canney .................. A61N 7/02 601/3 |
| 2011/0257523 | A1 | 10/2011 | Hastings |
| 2011/0282268 | A1 | 11/2011 | Baker et al. |
| 2012/0116221 | A1* | 5/2012 | Sehgal .................. A61N 7/00 600/439 |
| 2012/0259250 | A1 | 10/2012 | Sapozhnikov et al. |
| 2012/0302927 | A1 | 11/2012 | Khokhlova et al. |
| 2013/0018260 | A1 | 1/2013 | Sanghvi et al. |
| 2013/0041249 | A1 | 2/2013 | Salomir et al. |
| 2013/0158387 | A1* | 6/2013 | Tanttu ................ G01R 33/4804 600/411 |
| 2013/0217950 | A1* | 8/2013 | Partanen .................. A61N 7/02 601/2 |
| 2013/0225994 | A1 | 8/2013 | Hsu et al. |
| 2013/0317360 | A1* | 11/2013 | Hor .................. A61M 37/0092 600/431 |
| 2013/0345552 | A1 | 12/2013 | Arts et al. |
| 2014/0024922 | A1* | 1/2014 | Vijayvergia ........... A61B 5/055 600/411 |
| 2014/0058294 | A1 | 2/2014 | Gross et al. |
| 2014/0277032 | A1 | 9/2014 | Ahn et al. |
| 2014/0316269 | A1 | 10/2014 | Zhang et al. |
| 2014/0330175 | A1 | 11/2014 | Carol |
| 2015/0119763 | A1 | 4/2015 | Canney et al. |
| 2015/0359603 | A1* | 12/2015 | Levy .................. A61N 7/02 703/2 |
| 2017/0348040 | A1 | 12/2017 | Govari et al. |

OTHER PUBLICATIONS

Damianou, et al., "MRI monitoring of lesions created at temperature below the boiling point and of lesions created above the boiling point using high intensity focused ultrasound," Journal of Biomedical Science and Engineering, pp. 764-765, 767, 2010.

Khokhlova, et al., "Controlled tissue emulsification produced by high intensity focused ultrasound shock waves and millisecond boiling," J. Acoust. Soc. Am., 2011, v. 130(5), pp. 3498-3510, 2011.

Kim, et al., Volumetric MRI-HIFU ablation of uterine fibroids: role of treatment cell size in the improvement of energy efficiency, Eur J Radiol, vol. Nov. 81, No. 11, pp. 3652-3659, 2012.

Kohler, et al., "HIFU ablation under 3D guidance of rapid MRI thermometry," Med Phys., vol. 2009, vol. 36, No. 8, pp. 3521-3535, 2009.

Kreider, et al., "Characterization of a multi-element clinical HIFU system using acoustic holography and nonlinear modeling," IEEE Trans. Ultrason., Ferroelect., Freq. Contr., vol. 60, No. 8, pp. 1683-1698, 2013.

PCT/US15/23021 International Search Report and Written Opinion of the International Searching Authority, 30 pages, mailing date Sep. 29, 2015.

Maxwell, et al., "Disintegration of tissue using high intensity focused ultrasound: Two approaches that utilize shock waves," Acoustics Today, vol. 8, No. 4, pp. 24-36, 2012.

Simon, et al. "Ultrasonic atomization of tissue and its role in tissue fractionation by high intensity focused ultrasound." Physics in medicine and biology, vol. 57, No. 23, 8061-8078, 2012.

Wang, et al., "Histological and biochemical analysis of mechanical and thermal bioeffects in boiling histotripsy lesions induced by high intensity focused ultrasound." Ultrasound in medicine & biology, vol. 39, No. 3, pp. 424-438, 2013.

Khokhlova et al., "Stimulated Release of Nucleic Acid Cancer Biomarkers by Hifu: A Study in a Rat Prostate Cancer Model", Stimulated Release, Campus of SITU Shanghai, 2013, 1 page.

Keshavarzi et al., "Treatment of uterine fibroid tumors in an in situ rat model using high-intensity focused ultrasound", Fertility and Sterility, 2003, 80(2), 761-767.

Khokhlova et al., "HIFU for palliative treatment of pancreatic cancer", Journal of Gastrointestinal Oncology, 2011, 2(3), 175-184.

Khokhlova, et al., "Design of HIFU transducers to generate specific nonlinear ultrasound fields," pp. 1-6, Physics Procedia, 2016.

Khokhlova, et al., "Ultrasound-guided tissue fractionation by high intensity focused ultrasound in an in vivo porcine liver model," Proceedings of the National Academy of Sciences, vol. 111, No. 22, pp. 8161-8166, 2014.

Kreider, et al., "Rectified growth of histotripsy bubbles," Proceedings of Meetings on Acoustics, vol. 19, 4 pages, 2013.

Maxwell, et al., "A Prototype Therapy System for Transcutaneous Application of Boiling Histotripsy," IEEE Transactions on Ultrasonics, Ferroelectrics, and Frequency Control, 15 pages, 2016.

Maxwell, et al., "Probability Of Cavitation For Single Ultrasound Pulses Applied To Tissues And Tissue-Mimicking Materials," Ultrasound in Med. & Biol., vol. 39, No. 3, pp. 449-465, 2013.

PCT/US2015/023069 filed Mar. 27, 2015, Search Report and Written Opinion, 9 pages, 2015.

Picone, "Separatory Magnetic Transport (SMT) in Magnetic Resonance Force Moicroscopy: Theory & Experiment," University of Washington Department of Medical Engineering and Department of Orthopaedics, 15 pages, 2012.

Simon, et al., "2aBA9. Ultrasonic atomization: A mechanism of tissue fractionation," Proceedings of Meetings on Acoustics, vol. 19, 4 pages, 2013.

(56) References Cited

OTHER PUBLICATIONS

Simon, et al., "Investigation Into The Mechanisms Of Tissue Atomization By High-Intensity Focused Ultrasound," Ultrasound in Med. & Biol., vol. 41, No. 5, pp. 1372-1385, 2015.
Simon, et al., "Tissue Atomization by High Intensity Focused Ultrasound," IEEE International Ultrasonics Symposium Proceedings, pp. 1003-1006, 2012.
Simon, et al., "Ultrasonic atomization of liquids in drop-chain acoustic fountains," J Fluid Mech., vol. 766, pp. 12-146, 2015.
Simon, et al., "Ultrasonic atomization of tissue and its role in tissue fractionation by high intensity focused ultrasound," Physics in Medicine and Biology., vol. 57, pp. 8061-8078, 212.
Wang, et al., " Biomedical Acoustics Session 3aBAb: Generation and Detection of High Intensity Focused Ultrasound Lesions," Proceedings of Meetings on Acoustics, vol. 19, 3 pages, 2013.
Yuldashev, et al., "Characterization of nonlinear ultrasound fields of 2D therapeutic arrays," IEEE International Symposium Proceedings, pp. 925-928, 2012.
Kohler, et al., "Volumetric HIFU ablation under 30 guidance of rapid MRI thermometry," Med Phys., vol. 2009, vol. 36, No. 8, pp. 3521-3535, 2009.

\* cited by examiner

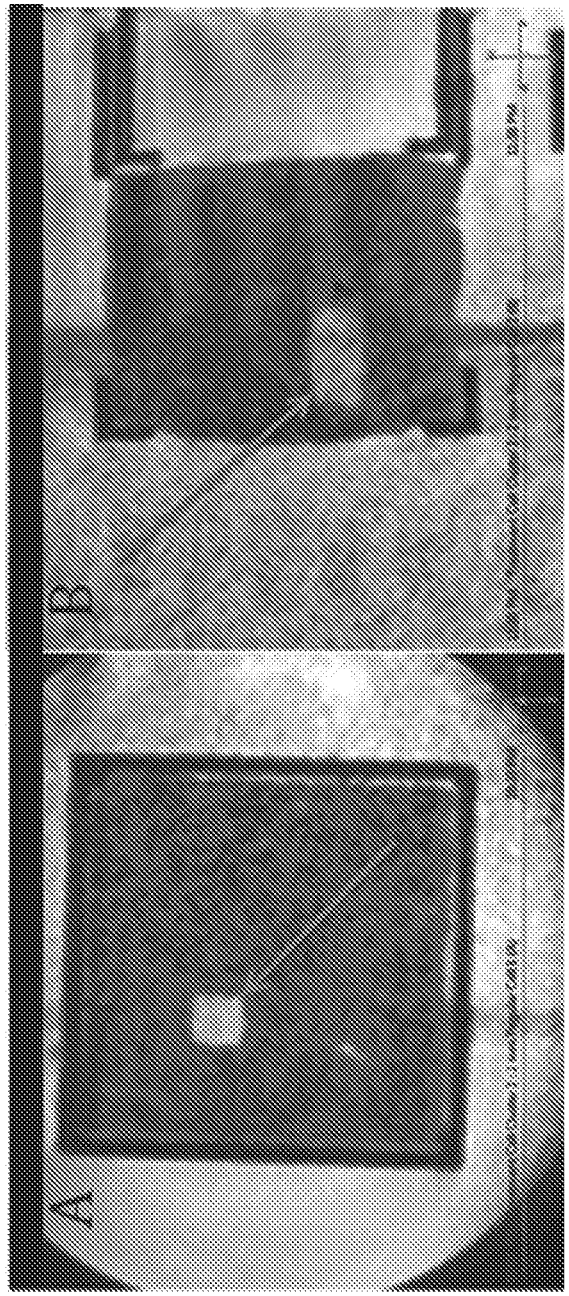

MRI-BASED FEEDBACK CONTROL OF ULTRASOUND BASED MECHANICAL FRACTIONATION OF BIOLOGICAL TISSUE

CROSS-REFERENCE TO RELATED APPLICATIONS

This application claims the benefit of U.S. application Ser. No. 15/737,670 filed on Dec. 18, 2017, which is a U.S. national phase of International Application No. PCT/US2016/038052 filed on Jun. 17, 2016, which claims priority to U.S. Provisional Application No. 62/181,448 filed Jun. 18, 2015, all of which are incorporated by reference herein in their entirety.

STATEMENT REGARDING FEDERALLY SPONSORED RESEARCH OR DEVELOPMENT

This invention was made with government support under Grant No. 2 R01 EB007643-05, awarded by the National Institutes of Health. The government has certain rights in the invention.

BACKGROUND

Unless otherwise indicated herein, the materials described in this section are not prior art to the claims in this application and are not admitted to be prior art by inclusion in this section.

High intensity focused ultrasound (HIFU) is a medical technology capable of transcutaneously fractionating or ablating selected portions of tissue without damaging intervening or surrounding tissues. In most HIFU applications, tissue is thermally ablated via heating caused by ultrasound energy absorption. Various techniques exist for using HIFU waves to fractionate, ablate, damage, or disintegrate diseased biological tissue or a foreign object within a patient. More specifically, energy carried by HIFU waves may be absorbed by a target region of tissue or absorbed by an object, so that the temperature of the target region or object is increased, causing thermal ablation. HIFU waves can also be sequentially focused (e.g., deflected or scanned) upon different target regions so that a larger macroscopic region of tissue or a large object may be thermally ablated. Techniques for HIFU-induced mechanical fractionation exist as well.

SUMMARY

In one example, a method includes displaying, via a user interface, an image representing first magnetic resonance imaging (MRI) data corresponding to biological tissue. The method further includes receiving, via the user interface, first input identifying one or more target regions of the biological tissue to be mechanically fractionated via exposure to first ultrasound waves. The method further includes applying the first ultrasound waves to the one or more target regions, thereby mechanically fractionating at least a portion of the one or more target regions. The first ultrasound waves are applied according to one or more first parameters. The method further includes, contemporaneous to or after applying the first ultrasound waves, acquiring second MRI data corresponding to the biological tissue. The method further includes determining, based on the second MRI data, one or more second parameters for applying second ultrasound waves to the biological tissue. The method further includes applying the second ultrasound waves to the biological tissue according to the one or more second parameters.

In another example, a non-transitory computer readable medium stores instructions that, when executed by a device, cause the device to perform functions. The functions include displaying, via a user interface of the device, an image representing first magnetic resonance imaging (MRI) data corresponding to biological tissue. The functions further include receiving, via the user interface, first input identifying one or more target regions of the biological tissue to be mechanically fractionated via exposure to first ultrasound waves. The functions further include applying, via a transducer of the device, the first ultrasound waves to the one or more target regions, thereby mechanically fractionating at least a portion of the one or more target regions. The first ultrasound waves are applied according to one or more first parameters. The functions further include, contemporaneous to or after applying the first ultrasound waves, acquiring, via an MRI imaging system of the device, second MRI data corresponding to the biological tissue. The functions further include determining, based on the second MRI data, one or more second parameters for applying second ultrasound waves to the biological tissue. The functions further include applying, via the transducer, the second ultrasound waves to the biological tissue according to the one or more second parameters.

In yet another example, a device includes one or more processors, a user interface, a transducer, a magnetic resonance imaging (MRI) system, and a non-transitory computer readable medium storing instructions that, when executed by the one or more processors, cause the device to perform functions. The functions include displaying, via the user interface, an image representing first MRI data corresponding to biological tissue. The functions further include receiving, via the user interface, first input identifying one or more target regions of the biological tissue to be mechanically fractionated via exposure to first ultrasound waves. The functions further include applying, via the transducer, the first ultrasound waves to the one or more target regions, thereby mechanically fractionating at least a portion of the one or more target regions. The first ultrasound waves are applied according to one or more first parameters. The functions further include, contemporaneous to or after applying the first ultrasound waves, acquiring, via the MRI imaging system, second MRI data corresponding to the biological tissue. The functions further include determining, based on the second MRI data, one or more second parameters for applying second ultrasound waves to the biological tissue. The functions further include applying, via the transducer, the second ultrasound waves to the biological tissue according to the one or more second parameters.

When the term "substantially" or "about" is used herein, it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide. In some examples disclosed herein, "substantially" or "about" means within +/−5% of the recited value.

These as well as other aspects, advantages, and alternatives will become apparent to those of ordinary skill in the art by reading the following detailed description, with reference where appropriate to the accompanying drawings. Further, it should be understood that this summary and other descriptions and figures provided herein are intended to illustrate the invention by way of example only and, as such, that numerous variations are possible.

BRIEF DESCRIPTION OF THE DRAWINGS

FIG. 3 is a simplified depiction of an image of biological tissue displayed by a user interface, in accordance with example embodiments.

FIG. 4 is a simplified depiction of an image of biological tissue with target regions that have been selected for mechanical fractionation, in accordance with example embodiments.

FIG. 11A is a real-time fast-field-echo (FFE) image of the ex vivo bovine liver tissue in the coronal plane.

FIG. 11B is a real-time FFE image of the ex vivo bovine liver tissue in the sagittal plane.

DETAILED DESCRIPTION

Figure 1:
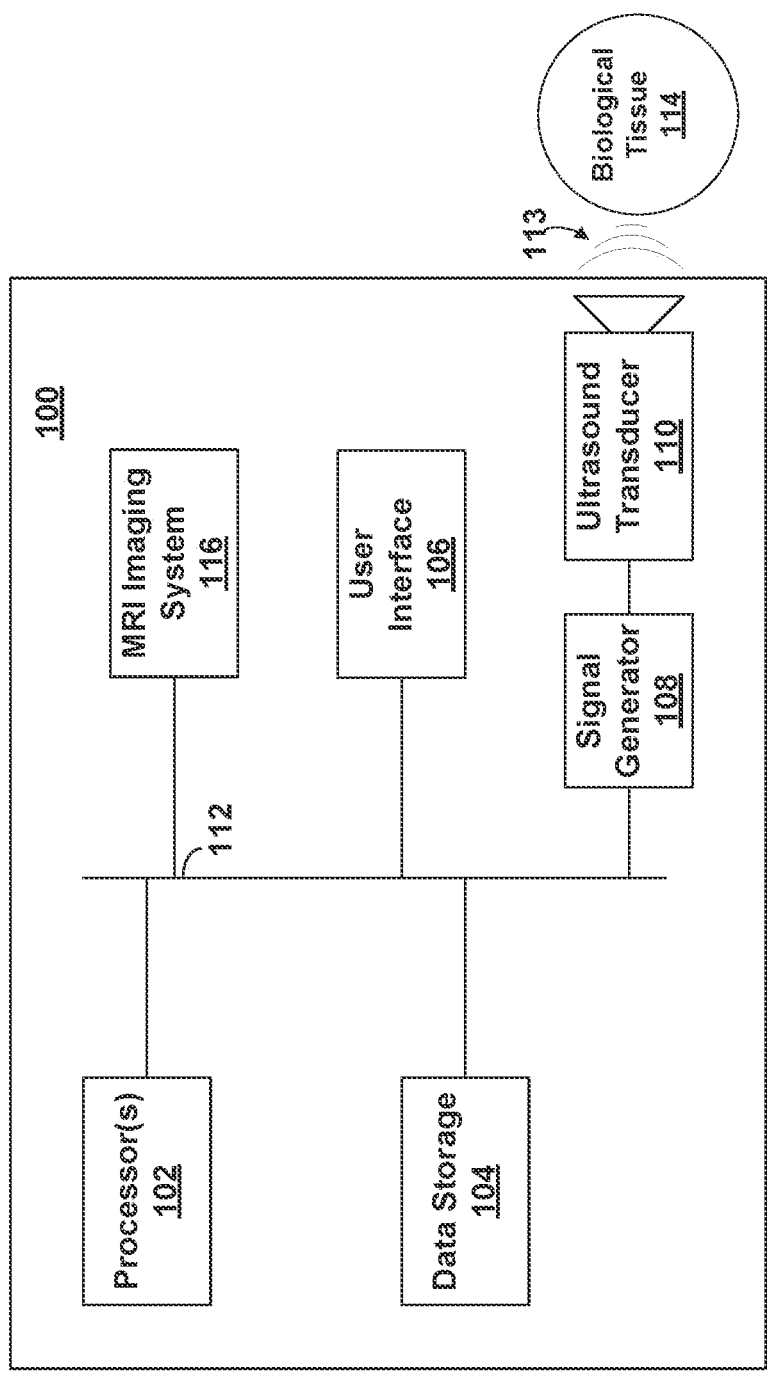
FIG. 1 is a schematic diagram of a device configured for mechanical fractionation of biological tissue or other objects, in accordance with example embodiments.

Although magnetic resonance imaging (MRI) and related MR diagnostic techniques can be used in conventional HIFU therapy, the purely thermal nature of conventional HIFU can limit the utility of MRI and MR techniques for monitoring, control, and diagnostic evaluation of HIFU when applied clinically or even experimentally. The limitations are largely due to diffusion of heat within biological tissue undergoing HIFU sonication. In particular, when biological tissue is subjected to HIFU sonication, diffusion of absorbed heat outward from a focal point of the HIFU sonication may render lesion formation somewhat imprecise and/or unpredictable. For example, the boundary between thermally ablated biological tissue and undisturbed tissue may drift outward from its intended location. Also, the boundary itself may lack sharpness, forming instead a possibly undesirable gradual transition from fully ablated tissue to undisturbed tissue surrounding the ablated tissue.

One result of the somewhat imprecise nature of conventional HIFU-induced lesion formation in biological tissue is a correspondingly imprecise ability to monitor and control lesion formation using HIFU in the first place. Another result is that MRI and MR techniques used in conjunction with HIFU for the purpose of control and evaluation of results can themselves be limited by gradation of contrast changes across lesion boundaries, for example. This, in turn, may diminish the evaluative utility of MR data acquired during and/or after HIFU sonication. Furthermore, the duration over which sonication induced heat diffuses away from the target region of the biological tissue may extend beyond the duration over which HIFU sonication is actually applied to the target region. Consequently, the volumetric extent of lesion formation may not be known until some time after HIFU sonication ceases. This can limit the utility of MRI and MR techniques for real-time monitoring of the effects of HIFU during sonication; the viability of evaluating the final lesion size may be similarly constrained.

Accordingly, there is a need for techniques that improve monitoring, control, and evaluation of HIFU-based targeted ablation or fractionation of biological tissue.

As such, an example method includes displaying, via a user interface, an image representing first magnetic resonance imaging (MRI) data corresponding to biological tissue. The method further includes receiving, via the user interface, first input identifying one or more target regions of the biological tissue to be mechanically fractionated via exposure to first ultrasound waves. The method further includes applying the first ultrasound waves to the one or more target regions, thereby mechanically fractionating at least a portion of the one or more target regions. The first ultrasound waves may be applied according to one or more first parameters. The method further includes, contemporaneous to or after applying the first ultrasound waves, acquiring second MRI data corresponding to the biological tissue. The method further includes determining, based on the second MRI data, one or more second parameters for applying second ultrasound waves to the biological tissue. The method further includes applying the second ultrasound waves to the biological tissue according to the one or more second parameters.

Disclosed herein are methods and devices for employing a novel adaptation of conventional HIFU that provides for better control and precision in targeted HIFU-induced ablation or fractionation of biological tissue. In accordance with example embodiments, HIFU may be adapted to cause targeted and controlled destruction of biological tissue by mechanical fractionation instead of by pure thermal ablation. This mechanical fractionation technique may enable destruction of one or more target regions of biological tissue with improved control. The technique may enable better control of the size and shape of the ablated portion of tissue, and better control of the location and definition of the boundary between ablated and non-ablated tissue. Post-sonication heat diffusion can typically be better managed via this mechanical fractionation technique.

In an example embodiment, an adapted HIFU technique termed "boiling histotripsy" (BH) is used for generating mechanically fractionated lesions in biological tissue. BH is a therapeutic technique in which lesions can be purely mechanical in origin, i.e. liquefied, or, in addition to mechanical fractionation, include different degrees of thermal effect controlled by the parameters of an ultrasound exposure (sonication) protocol. Specifically, the peak output power, resultant in situ shock amplitude, ultrasound frequency, pulse length, pulse repetition rate, number of pulses, and sonication trajectory can be adjusted.

In one example demonstration, BH sonication was performed volumetrically, i.e., involving concurrently or sequentially sonicating regions larger than a single focal point. In another example demonstration, various MRI methods were used to monitor BH sonication in real time, as well as assess the therapy outcome.

MRI can provide in vivo anatomical, functional, and temperature images, as well as provide information on tissue displacement in real time during a HIFU sonication. While MRI-based feedback can be used to control conventional MR-HIFU thermal ablation, (e.g., to achieve complete thermal necrosis in the target region), as well as to control conventional MR-HIFU mediated mild hyperthermia, these techniques rely on the monitoring of HIFU-induced temperature changes only.

The BH method can be used to induce mechanically-fractionated lesions with a controlled degree of thermal effect. The technique may involve repetitive millisecond-long pulses with shocks, rapid localized boiling in tissue caused by shock wave heating, and interaction of shocks with a vapor cavity. Such an approach can be advantageous for avoiding overheating of vessels, bone, or other structures located close to the treatment site. This approach may also accelerate resorption or passage of the ablated tissue volume, diminish pressure on the surrounding organs that causes discomfort, and insert openings between tissues, among other desired effects or outcomes.

Some benefits enabled by BH are the ability to use MRI to accurately plan BH-sonications, to perform BH-therapy under real-time imaging guidance, and to evaluate the outcome of the treatment.

In conventional HIFU, the extent of a thermally coagulated region may be estimated based on accumulated thermal dose, and might not accurately reflect the final post-therapy outcome. Similarly, in mild hyperthermia, temperature in the target region may be elevated to 40-45° C. for a prolonged duration, after which the tissue is allowed to cool down. The region of mild hyperthermia may be estimated from the temperature gradients and/or thermal dose over time. However, tissue contrast changes are not easily seen via MR-imaging when used in conjunction with either thermal ablation or mild hyperthermia.

In contrast, various MRI methods can be used during BH-mediated mechanical tissue fractionation to monitor and control progress of BH in real time based on tissue contrast changes. For example, during BH therapy, real-time imaging findings can provide a basis for adjusting the sonication power, duty cycle, duration, number of pulses, and/or sonication trajectory for more desirable results (e.g., full mechanical fractionation of tissue at the target location). In addition to monitoring contrast changes in real time, temperature can be monitored simultaneously inside and outside of the target region to avoid exceedingly high temperatures at the target as well as avoid temperature elevations and tissue damage outside of the target region. Use of MRI and MR techniques in conjunction with BH (and HIFU histotripsy in general) to plan, monitor, control, and evaluate BH-induced targeted destruction of biological tissue prior to, during, and after BH sonication is referred to herein as "MRI-assisted BH."

The term "biological tissue" is used herein to refer generically to tissue such as human (or other animal) tissue and/or organs, as well as other tissue of biological origin. Biological tissue (human or other) can be part of a living or non-living subject. For example, in some of the discussions below, demonstration operations of MRI-assisted BH were applied to sample biological tissue including ex vivo bovine liver and heart tissue. Other non-limiting examples of "biological tissue" used herein include liver tissue, uterine tissue, kidney tissue, prostate tissue, thyroid tissue, pancreas tissue, brain tissue, nerve tissue, connective tissue, fat tissue, or muscle tissue. Biological tissue can also include a biological substance, such as a blood clot or a hematoma.

The terminology "targeted destruction of biological tissue" used herein is generally synonymous with controlled and/or intentional lesion formation in tissue and/or organs, although the result of such intentional "destruction of biological tissue" may not necessarily be a lesion. Further, MRI-assisted BH can be applied to treatment of pathological tissue, such as malignant tumors and/or benign tumors, where non-limiting examples of benign tumors include an adenoma or a fibroid. Additionally, MRI-assisted BH can used to create and/or insert of openings in biological tissue for various therapeutic purposes.

It should be noted that various changes and modifications to the presently preferred embodiments described herein will be apparent to those skilled in the art. Such changes and modifications may be made without departing from the spirit and scope of the present invention and without diminishing its attendant advantages.

Referring now to the Figures, FIG. 1 illustrates an example device (or system) 100 configured to mechanically fractionate biological tissue 114 (or other objects) using an acoustic ultrasound wave (or "HIFU" wave) 113. The device 100 includes one or more processors 102, data storage 104, a user interface 106, a signal generator 108, an ultrasound transducer 110, and a magnetic resonance imaging (MRI) system 116, any or all of which may be communicatively coupled to each other via a system bus or another connection mechanism 112.

The processor(s) 102 may include a general purpose processor and/or a special purpose processor and may be configured to execute program instructions stored within data storage 104. In some examples, the processor(s) 102 may be a multi-core processor comprised of one or more processing units configured to coordinate to execute instructions stored within data storage 104. In one example, the processor(s) 102, by executing program instructions stored within data storage 104, may provide ultrasound parameters to the signal generator 108 for generation of ultrasound waves. In another example, the processor(s) 102 may provide, to the signal generator 108, ultrasound parameters that are received via the user interface 106.

Data storage 104 may include one or more volatile, non-volatile, removable, and/or non-removable storage components. Data storage 104 may include a magnetic, optical, or flash storage medium, and may be integrated in whole or in part with the processor(s) 102 or other portions of the device 100. Further, the data storage 104 may be a non-transitory computer-readable storage medium, having stored thereon program instructions that, when executed by the processor(s) 102, cause the device 100 to perform any function described in this disclosure. Such program instructions may be part of a software application that can be executed in response to inputs received from the user interface 106, for instance. The data storage 104 may also store other types of information or data, such as those types described throughout this disclosure.

The user interface 106 may enable interaction with a user of the device 100, if applicable. The user interface 106 may include input components such as a keyboard, a mouse, a keypad, a touchscreen, or a touch-sensitive panel, and output components such as a display screen (which, for example, may be combined with a touch-sensitive panel), a sound speaker, or a haptic feedback system. In one example, the user interface 106 may receive input indicating various parameters for an ultrasound wave to be generated by the ultrasound transducer 110.

The signal generator 108 may be configured to receive, from the processor(s) 102, data indicative of ultrasound parameters for generation of an ultrasound wave by the ultrasound transducer 110. For example, the processor(s) 102 may send, to the signal generator 108, data representative of input received via the user interface 106. In another example, the received input may simply indicate one of several predetermined ultrasound fractionation protocols represented by program instructions stored at data storage 104. In other instances, the ultrasound fractionation protocols may be selected automatically by the processor(s) 102 based on MRI data received from the MRI imaging system 116. Such data received by the signal generator 108 may indicate various ultrasound parameters such as power, power density, intensity, oscillation frequency, pulse duration, duty cycle, and a number of pulses to be generated for various portions of the biological tissue 114. The received data may also indicate a trajectory, path, or sequence of portions of the biological tissue 114 upon which the focal point of the ultrasound wave may be sequentially directed upon. In some examples, multiple ultrasound beams may be focused on multiple regions of biologic tissue simultaneously. The received data may also include timing information indicating when and/or for how long the focal point of the ultrasound wave should be directed upon each respective portion of the biological tissue 114.

The ultrasound transducer 110 may include an array of one or more piezoelectric transducer elements or a lithotripter configured to generate ultrasound or other acoustic waves in response to receiving control signals representing ultrasound parameters from the signal generator 108. For example, the ultrasound transducer 110 may include a phased array of transducer elements configured to electronically focus or steer a generated ultrasound wave upon various portions of the biological tissue 114 via constructive and/or destructive wave interference. Each transducer element of the ultrasound transducer 110 may receive its own independent control signal from the signal generator 108. In some examples, the signal generator 108 and the ultrasound transducer 110 may be integrated into one functional unit. The ultrasound transducer 110 may include one or more of (i) a lens, (ii) one or more transducers having a radius of curvature at the focal point of the ultrasound wave, and (iii) a phased array of transducers.

Some examples of forms the biological tissue 114 may take include a tumor, a hematoma, an abscess, a lipoma, or any other diseased or undesirable tissue. The biological tissue may also include any combination of one or more of the following types of tissues: liver, uterus, kidney, prostate, brain, breast, heart, blood vessel, lung, fat, nerve, or pancreas. Other examples are possible.

Generally, the device 100 may be used to fractionate any object or tissue. It should be assumed that for any example disclosed herein involving biological tissue, a generic object may be substituted in place of the biological tissue. In these examples, the object might take the form of a foreign object within a living body, but other examples are possible.

The MRI Imaging system 116, as is known in the art, may include superconductive magnets, gradient coils, and/or RF transmission and reception coils, among other components. The MRI imaging system 116 may take the form of a Philips Achieva 3T clinical MR scanner. In other examples, the MRI imaging system 116 may take the following forms as well: Philips Ingenia, Philips Multiva, Siemens Magnetom, GE Signa, GE Optima, GE Discovery, Toshiba Vantage, Hitachi Echelon, or Hitachi Oasis. Other examples are possible. The MRI imaging system 116 may be configured to use the superconductive magnets (or other means) to apply a static magnetic field to biological tissue or other material under examination. The static magnetic field may align the spin of many or most hydrogen nuclei (i.e., protons) within the biological tissue to be parallel with a single axis. (Nuclei of atoms other than hydrogen may be imaged as well.) The transmission coils (or other means) may be used to apply a time-varying (e.g., RF) magnetic field, thereby realigning the spins of at least some of the hydrogen nuclei away from the axis of the static field. When the RF field is relaxed, the reception coils (or other means) may detect RF waves emitted from the biological tissue as the hydrogen nuclei relax to be again aligned with the static magnetic field. This process may be repeated periodically in real time to generate images of the biological tissue. By mapping the RF data to the location at which it was detected, images can be generated by the MRI imaging system 116 and displayed by the user interface 106.

Figure 2:
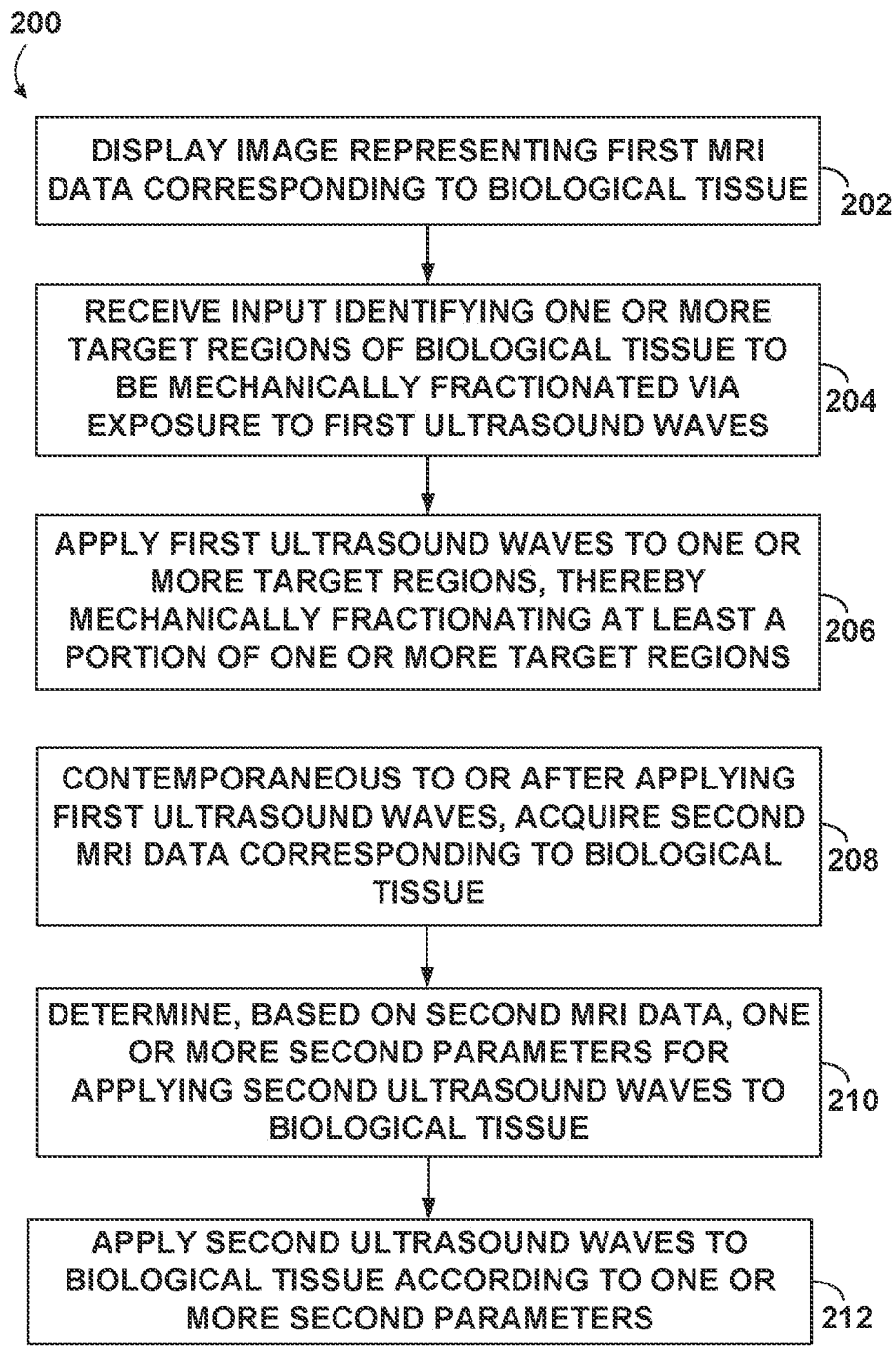
FIG. 2 is a flow chart depicting an example method for mechanical fractionation of a volume within biological tissue or other objects, in accordance with example embodiments.

FIG. 2 is a flow chart depicting an example method 200 for mechanically fractionating biological tissue or other objects. The method 200 depicted in FIG. 2 presents an example method that can be performed using the device 100. In other examples, the method 200 may be performed via any combination of suitable components described herein. FIG. 2 may include one or more operations, functions, or actions as illustrated by one or more of blocks 202, 204, 206, 208, 210, and 212. Although the blocks are illustrated in a sequential order, these blocks may in some instances be performed in parallel, and/or in a different order than those described herein. Also, the various blocks may be combined into fewer blocks, divided into additional blocks, and/or removed based upon the desired implementation.

In addition, for the method 200, and other processes and methods disclosed herein, the flowcharts show functionality and operation of one possible implementation of present embodiments. In this regard, each block may represent a module, a segment, or a portion of program code, which includes one or more instructions executable by a processor for implementing specific logical functions or steps in a process. The program code may be stored on any type of computer readable medium, for example, such as a storage device including a disk or hard drive. The computer readable medium may include a non-transitory computer readable medium, for example, such as computer readable media that stores data for short periods of time like register memory, processor cache, or Random Access Memory (RAM). The computer readable medium may also include non-transitory media, such as secondary or persistent long term storage, like read-only memory (ROM), optical or magnetic disks, or compact-disc read-only memory (CD-ROM), for example. The computer readable media may also be any other volatile or non-volatile storage system. The computer readable medium may be considered a computer readable storage medium, a tangible storage device, or other article of manufacture, for example.

In addition, for the method 200, and other processes and methods disclosed herein, each block in FIG. 2 may represent circuitry that is wired to perform the specific logical functions in the process.

Figure 3:
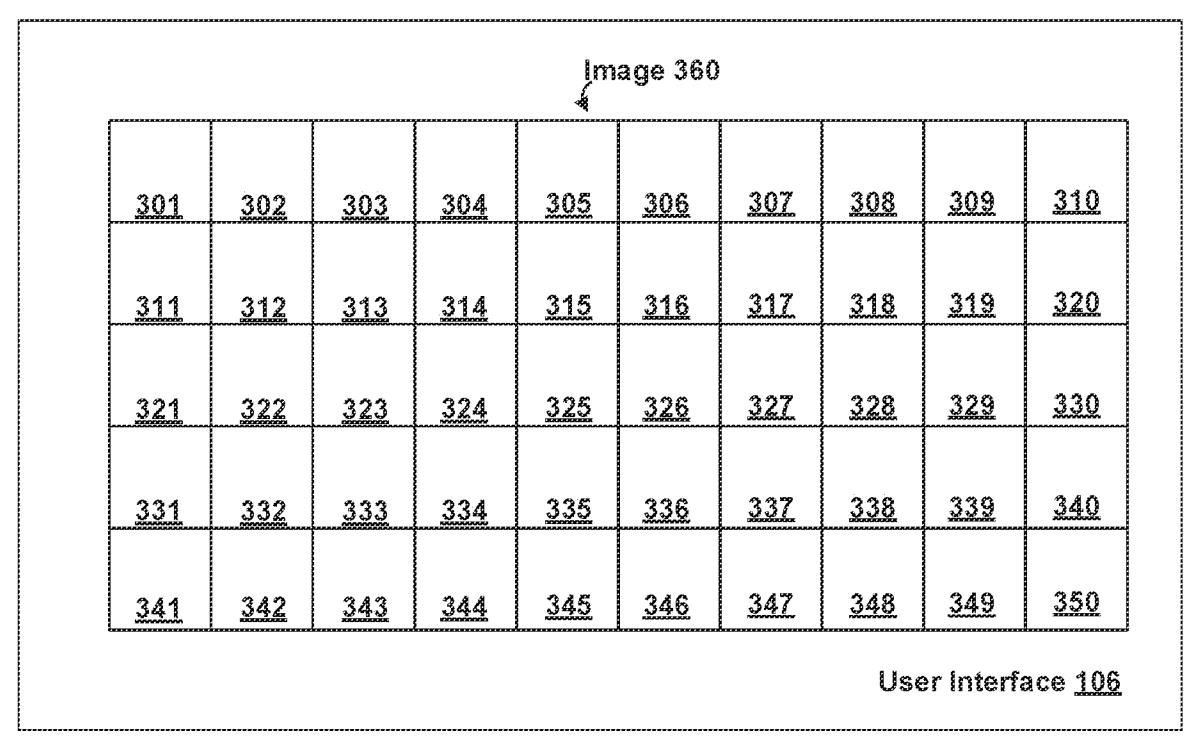

At block 202, the method 200 involves displaying, via a user interface, an image representing first magnetic resonance imaging (MRI) data corresponding to biological tissue. As depicted in FIG. 3, for example, the user interface 106 may display an image 360 representing first MRI data corresponding to the biological tissue 114. Prior to the user interface 106 displaying the image 360, the MRI imaging system 116 may acquire the first MRI data depicted by the image 360. In other examples, the first MRI data may be acquired by the MRI imaging system 116 or another MRI system during a previous imaging session. As shown in FIG. 3, the image 360 (i.e., the biological tissue 114) is arbitrarily apportioned into regions 301-350 for the purpose of explaining concepts below.

The first MRI data may include any combination of one or more of the following: diffusion-weighted MRI data, tissue elasticity data, temperature data, T1-weighted data, T2-weighted data, proton density weighted data, magnetic resonance elastography (MRE) data, magnetic resonance acoustic radiation force imaging (MR-ARFI) data, T1 mapping data, T2 mapping data, contrast-enhanced MRI data, tissue displacement data, perfusion weighted imaging data, T2-star (T2*) weighted imaging data, T2* mapping imaging data, an apparent diffusion coefficient (ADC) map, or thermal dosage data. The first MRI data may take other forms as well.

Figure 4:
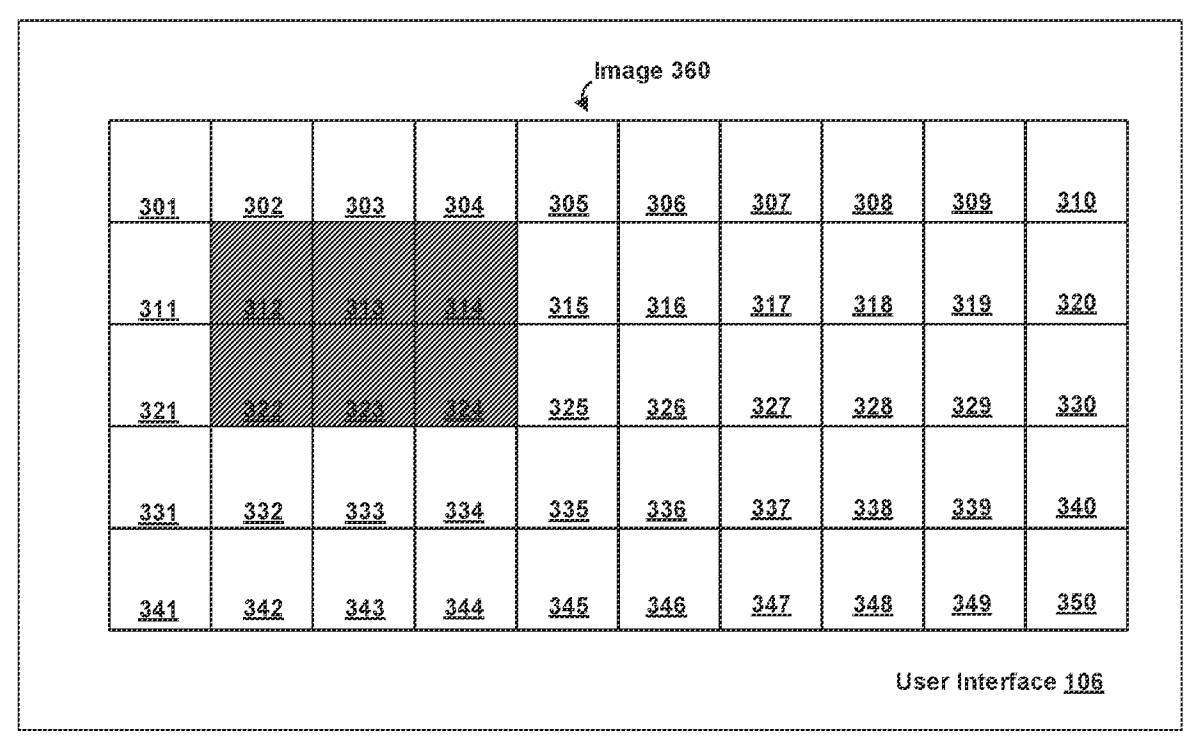

At block 204, the method 200 involves receiving, via the user interface, first input identifying one or more target regions of the biological tissue to be mechanically fractionated via exposure to first ultrasound waves. For example, the user interface 106 may receive, via a mouse, touchscreen, or another user input device of the user interface 106, first input identifying portions 312, 313, 314, 322, 323, and 324 of the biological tissue 114 for mechanical fractionation, as indicated by shading in FIG. 4.

Herein, the term "mechanical fractionation" may include processes in which ultrasound waves cause some degree of thermal ablation of the targeted tissue or object, although in many instances it will be beneficial if the damage inflicted on the targeted tissue or object is mostly mechanical in nature.

In some examples, the first input itself may indicate the respective boundaries of the regions 312, 313, 314, 322, 323, and 324. For instance, a user might use a mouse or a touchscreen to encircle respective boundaries of the regions 312, 313, 314, 322, 323, and 324. In another example, the first input might indicate a perimeter that collectively encircles the regions 312, 313, 314, 322, 323, and 324. In other examples, the first input may indicate a selection of a pre-defined boundary template whereby the first input also indicates positioning of the predefined boundary template upon the image 360. In accordance with the example of FIG. 4, the first input might take the form of a selection of a pre-defined rectangular boundary. The first input might further indicate a size and a desired position of the pre-defined boundary (e.g, via a click and drag gesture). In other examples, the user-defined boundary might be circular or take other shapes as well. Although not depicted in FIG. 4, the one or more target regions may, in practice, take the form of one or more target volumes. That is, the first input may indicate one or more three-dimensional regions for mechanical fractionation. In this context, the user interface 106 may display images of the biological tissue 114 in more than one image plane to facilitate selection of three-dimensional volumes of the biological tissue 114.

At block 206, the method 200 involves applying the first ultrasound waves to the one or more target regions, thereby mechanically fractionating at least a portion of the one or more target regions. Mechanical fractionation may be intended to include physical effects such as liquification and/or deformation of tissues or objects, among other physical effects. Mechanical fractionation may occur via boiling histotripsy and/or cavitation histotripsy, among other techniques. The first ultrasound waves may be applied using the ultrasound transducer 110, for example. The first ultrasound waves may take the form of a beam that is selectively and/or sequentially focused upon the regions 312, 313, 314, 322, 323, and 324. In this context, the first ultrasound waves may be applied according to one or more first parameters.

The one or more first parameters of the first ultrasound waves may include any combination of one or more of: a sonication trajectory (e.g., path), a sequence upon which the first ultrasound waves are focused respectively upon each of the one or more target regions, a quantity of consecutive or non-consecutive pulses that may be focused respectively upon each of the one or more target regions, pulse durations, duty cycle, pulse repetition frequency, oscillation frequency, power level, or intensity. The one or more first parameters may be indicated as part of the first input received via the user interface 106, but other examples are possible.

Figure 5:
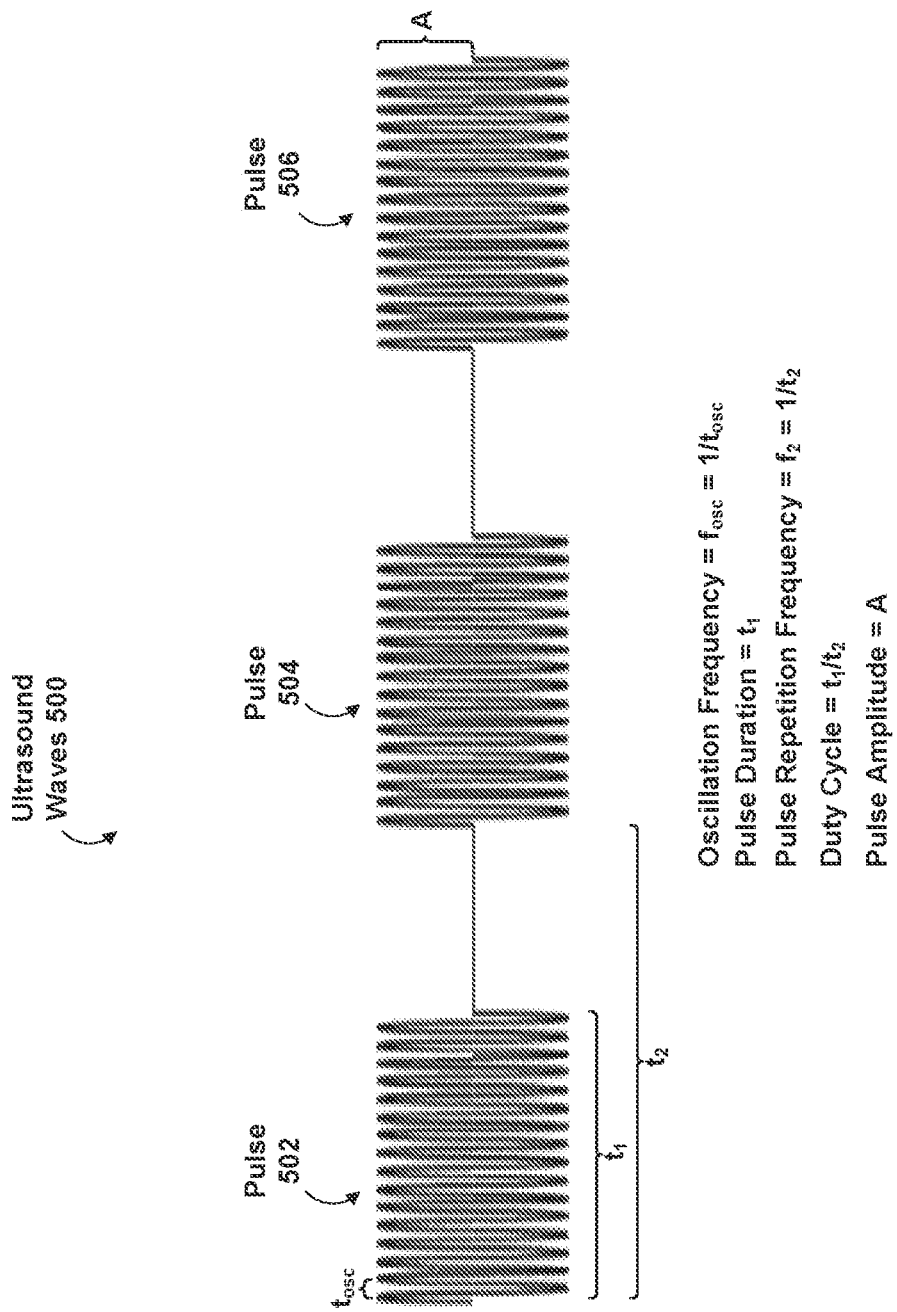
FIG. 5 is an illustration of emitted ultrasound pulses defined by several parameters, in accordance with example embodiments.

FIG. 5 depicts some example parameters that may define the first ultrasound waves (or the second ultrasound waves discussed below). Ultrasound waves 500 may take the form of one or more pulses, such as pulses 502, 504, and 506. Each of the pulses 502-506 may have an oscillation frequency $f_{osc}$, pulse duration $t_1$, pulse repetition frequency $f_2$, and/or a duty cycle $t_1/t_2$ as illustrated by FIG. 5. The pulses 502-506 may have a power level defined at least in part by an amplitude "A." A power density level (e.g., intensity, $W/cm^2$) defining the pulses 502-506 may also account for the spatial distribution of the ultrasound power embodied by the pulses 502-506 (e.g., beamwidth).

At block 208, the method 200 involves, contemporaneous to or after applying the first ultrasound waves, acquiring second MRI data corresponding to the biological tissue. The acquired second MRI data may reflect physical effect(s), if any, that the first ultrasound waves have upon the biological tissue 114. Acquiring the second MRI data (or the first MRI data) may include any technique known in the art for using an MRI imaging system, the technique being suitable for acquiring the many forms MRI data may take as described above.

At block 210, the method 200 involves determining, based on the second MRI data, one or more second parameters for applying second ultrasound waves to the biological tissue. In many cases, the second ultrasound waves might be applied immediately after the first ultrasounds waves, reflecting a real-time MRI feedback process. In one example, fractionation of the one or more target regions may be proceeding as expected, and the one or more second parameters might be selected to be the same as the one or more first parameters. That is, it may be determined that no corrective action is required based on monitoring of the progress of the fractionation of the biological tissue 114 via the first ultrasound waves. In other examples, fractionation of the one or more target regions via the first ultrasound waves might not be proceeding as expected, and a suitable adjustment to the sonication trajectory or parameters may be in order. The determined one or more second parameters may include parameters similar to any of the examples provided above for the one or more first parameters of the first ultrasound waves. In some examples, the one or more second parameters may be indicated by second input received via the user interface 106 (e.g., after viewing of the effects of the first ultrasound waves) and the processor may assign the one or more second parameters to the second ultrasound waves accordingly.

Figure 6:
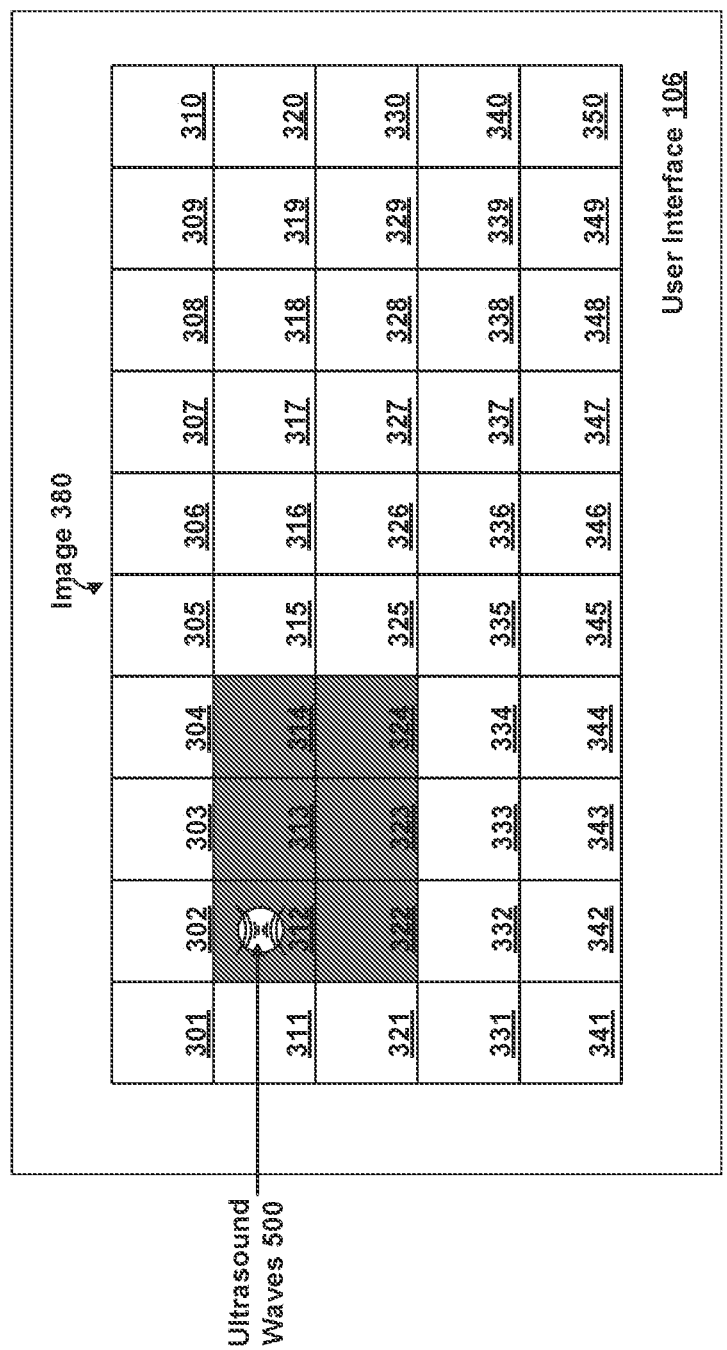
FIG. 6 is a simplified depiction of an image of biological tissue that has undergone a portion of a mechanical fractionation procedure, in accordance with example embodiments.

FIG. 6 shows the user interface 106 displaying an image 380. The image 380 may be a real-time MRI image of the biological tissue 114 as the ultrasound waves 500 are being applied to the target region 312 of the biological tissue 114. In other examples, the image 380 may be an image of the biological tissue 114 sometime after the first ultrasound waves have been applied to the biological tissue 114. FIG. 6 depicts the region 312 as being at least partially mechanically fractionated.

In some examples, a user might view the image 380 and determine the one or more second parameters for upcoming sonication based on certain characteristics of the biological tissue 114 shown in the image 380. For instance, the user might decide that the first ultrasound waves fractionated the region 312 too quickly, and decide that the second ultrasound waves should be applied to the region 313 with a lower power setting than the first ultrasound waves. In another example, the user might determine that the focus of the first ultrasound waves is too wide and decide that the focus of the second ultrasound waves should be narrower than the first ultrasound waves.

In yet another example, the user might operate the ultrasound transducer 110 according to three criteria: (1) stopping or pausing sonication of the region 312 or refocusing ultrasound waves upon another target region of the treatment trajectory if an MRI signal intensity corresponding to the region 312 exceeds a threshold corresponding to a suitable degree of mechanical fractionation, (2) stopping or pausing sonication if a temperature indicated by the second MRI data indicates a temperature of the biological tissue 114 that exceeds a threshold temperature, and (3) stopping sonication of the biological tissue 114 as a whole if a maximum duration of sonication is exceeded. Many other examples are possible. In the absence of detecting an event like those described above, sonication may proceed according to the one or more first parameters without adjustment. In other examples, the processor(s) 102 may automatically make such determinations and adjust the sonication protocol accordingly. That is, the one or more second parameters for the second ultrasound waves may be determined either automatically by the processor(s) 102 or manually via input received by the user interface 106.

Ultrasound parameters may be adjusted based on many other action criteria as well. Such parameters may include any combination of one or more of peak output power, peak acoustic pressure (e.g., either at the focus or at the transducer), oscillation frequency, duty cycle, pulse duration, pulse repetition rate, or trajectory. Other examples are possible.

In some examples, the first input received by the user interface 106 may also indicate one or more characteristics of the second MRI data for evaluation. For example, the first input might indicate (1) MRI signal intensity of region 312 and (2) the temperature of the region 338 indicated by the second MRI data as criteria of the second MRI data to be evaluated. The first input may further include commands to: (1) stop or pause sonication of the region 312 or refocus ultrasound waves upon another target region of the treatment trajectory if the MRI signal intensity corresponding to the region 312 exceeds a threshold corresponding to a suitable degree of mechanical fractionation, (2) stop or pause sonication if the temperature corresponding to target region 338 exceeds a threshold temperature, and (3) stopping sonication of the biological tissue 114 as a whole if a maximum duration of sonication is exceeded. The processor(s) 102 may determine the one or more second parameters based on evaluating the characteristics of the second MRI data identified by the first input. Such characteristics of the second MRI data may include signal intensity, proton signal intensity, T1 signal intensity, T2 signal intensity, indicated temperature, indicated tissue diffusivity, indicated tissue elasticity, or indicated tissue deformation. The one or more second parameters may also be determined based on a total ultrasound exposure duration or a total sonication energy absorbed by the biological tissue.

At block 212, the method 200 involves applying the second ultrasound waves to the biological tissue according to the one or more second parameters. Block 212 may be similar to block 206 with the possible exception that the one or more second parameters might be different from the one or more first parameters as described above. In other examples, the one more first parameters might be equal to the one or more second parameters.

Figure 7:
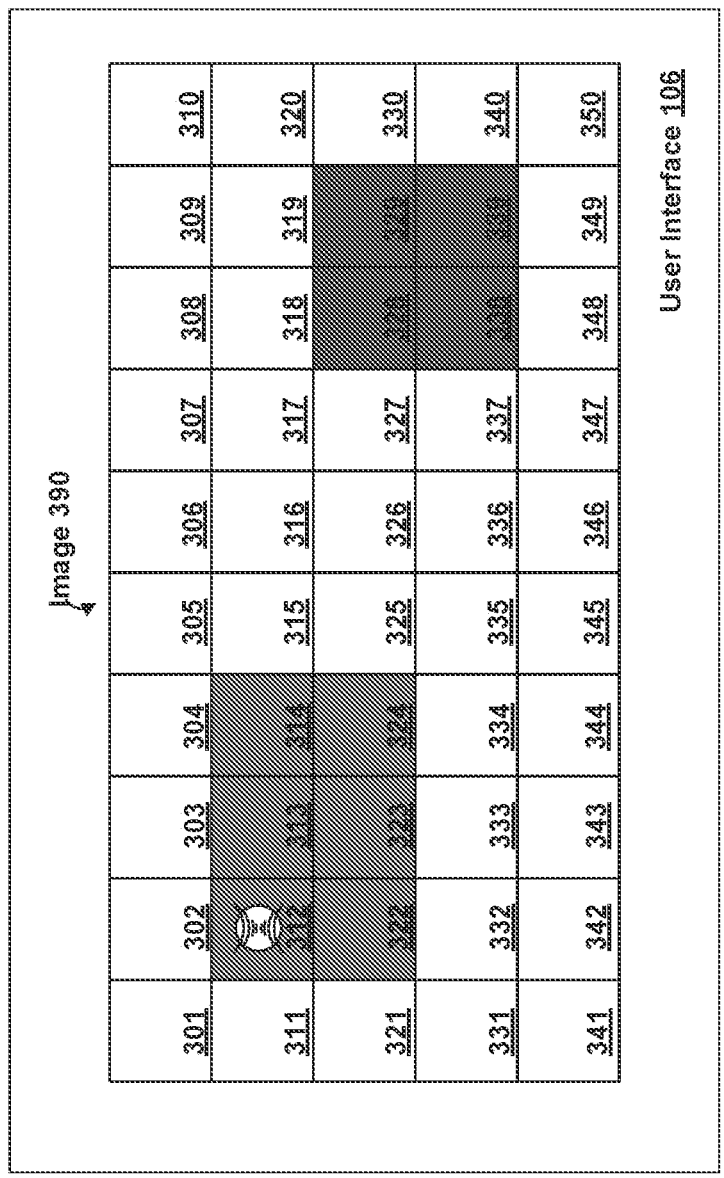
FIG. 7 is a simplified depiction of an image of biological tissue with avoidance regions that have been selected for monitoring during mechanical fractionation of target regions, in accordance with example embodiments.
Figure 8:
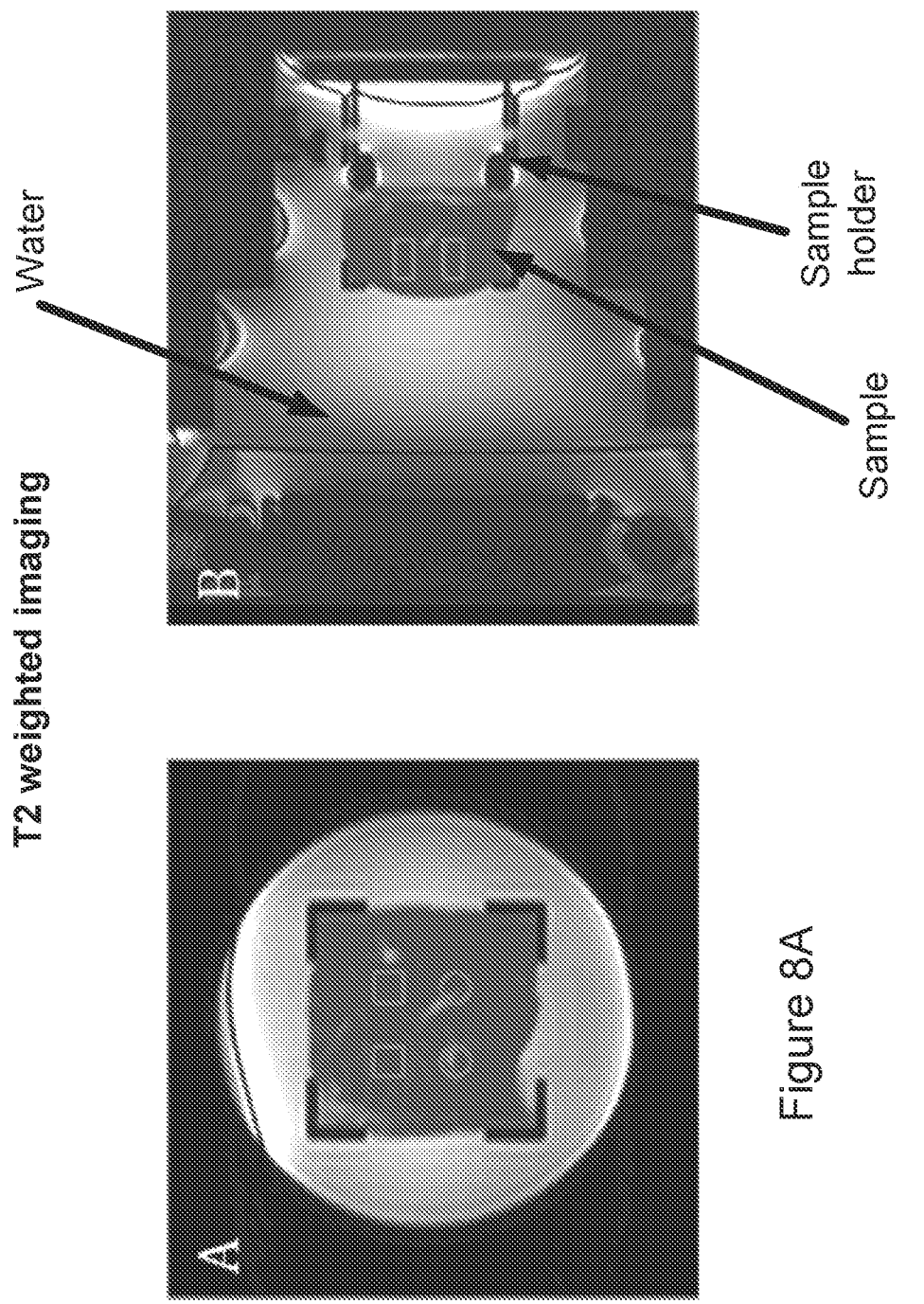
FIG. 8A is a T2-weighted MRI image of ex vivo bovine liver tissue in the coronal image plane with target regions shown.
FIG. 8B is a T2-weighted MRI image of ex vivo bovine liver tissue in the sagittal image plane with target regions shown.

Additional features of example embodiments are described below. FIG. 7 shows an image 390 of the biological tissue 114. Avoidance regions 328, 329, 338, and 339 are shown in a shade of gray that is darker than that of the target regions 312, 313, 314, 322, 323, and 324. In some examples, the avoidance regions 328, 329, 338, and 339 may include tissues such as bone, muscle, skin, blood vessels, nerves, bowels, lungs, or other organs for which sonication is not intended and for which overheating or other damage is undesirable.

In some examples, characteristics of a portion of the second MRI data corresponding to the avoidance regions 328, 329, 338, and 339 may be evaluated. This may involve characteristics such as signal intensity, proton signal intensity, T1 signal intensity, T2 signal intensity, indicated temperature, indicated tissue diffusivity, indicated tissue elasticity, or indicated tissue deformation.

By further example, the first input received by the user interface 106 may also indicate the avoidance regions 328, 329, 338, and 339 as regions to be monitored while the target regions 312, 313, 314, 322, 323 are sonicated. The input identifying the avoidance regions may be similar to the input that indicates the target regions 312, 313, 314, 322, 323, and 324. The first input may further indicate particular characteristics of the MRI data corresponding to the avoidance regions 328, 329, 338, and 339 to be evaluated.

For instance, the first input may further indicate that a signal intensity of the second MRI data corresponding to the avoidance region 338 should be monitored. As sonication of the target regions 312, 313, 314, 322, 323, and 324 proceeds, the processor may evaluate the MRI data corresponding to the avoidance region 338 in real-time, and may pause sonication or redirect the ultrasound beam if the signal intensity corresponding to the avoidance region 338 exceeds a threshold value. In another example, the processor may evaluate the MRI data corresponding to the avoidance region 338 in real-time, and may pause sonication or redirect the beam (e.g., away from the avoidance region 338) if the temperature corresponding to the avoidance region 338 exceeds a threshold temperature (e.g., 43° C.).

The following is description of another example that utilizes some of the concepts described above. One of skill in the art will realize that many other examples are contemplated herein.

First, a user may use the MRI imaging system 116 to acquire MRI data corresponding to a biological tissue. The user interface 106 may display an image representing the acquired MRI data. Next, the user may provide input via the user interface 106 indicating a two-dimensional or three-dimensional region of interest (ROI) of approximately 1 cm in diameter, centered on a target location. The processor(s) 102 may generate (e.g., calculate) one or more treatment trajectories for boiling histotripsy within the ROI, with user-prescribed separation between the points and trajectories. The user interface 106 might also receive input indicating two-dimensional ROIs in the near field, and in the far field, to indicate regions in which high temperature elevations should be avoided. The processor(s) 102 may use these latter ROIs to define avoidance regions.

A sonication protocol may be determined such that if a T1 signal intensity of the ROI in the target region exceeds a threshold signal intensity, the ultrasound transducer 110 may halt sonication. In a similar fashion, if signals corresponding to temperatures that exceed a threshold are detected from the avoidance regions, the ultrasound transducer 110 may halt sonication. Lastly, the ultrasound transducer 110 may halt sonication if a total sonication duration exceeds a threshold duration. Input received by the user interface 106 may define the threshold signal intensity, the threshold temperature, and/or the threshold duration discussed above. The input received via the user interface 106 may also define any other parameter that characterizes ultrasound waves to be generated during the sonication.

As the sonication begins, the processor(s) 102 receives MRI data acquired by the MRI imaging system 116. The processor(s) 102 adjusts the parameters of the sonication based on the acquired MRI data and causes the ultrasound transducer 110 to sonicate the biological tissue 114 accordingly. The processor(s) 102 may repeatedly use the acquired MRI data to compare the actual T1 signal intensity within the target region to the predetermined minimum T1 signal intensity. The processor(s) 102 may also repeatedly use the acquired MRI data to compare the actual temperature of the avoidance region to the predetermined threshold temperature. The processor(s) 102 may repeatedly modify the sonication protocol according to the criteria defined above.

FIGS. 8-14 illustrate experiments that were performed to demonstrate the functionality of the aforementioned methods, devices, and systems.

FIG. 8A is a coronal cross-section of a portion of ex vivo bovine liver tissue. FIG. 8B is a sagittal cross-section of the same liver tissue that is depicted in FIG. 8A. The images of FIGS. 8A and 8B were used to plan an experimental protocol for sonicating the liver tissue. The ultrasound beam generated by a transducer was steered from left to right with respect to FIG. 8B. The images of FIGS. 8A and 8B can be used for planning of a sonication therapy. For example, regions-of-interest (ROI) for feedback control can be defined both within the target region (depicted by rectangles and circles) and/or outside of the target region. For example, an ROI within the target region can be used to stop therapy once the diameter of the lesion as seen in real time exceeds 1 cm. Similarly, an ROI in the near field can be used to pause therapy once the temperature within this ROI exceeds, e.g., 43 C. The volume of the ROIs in this example are 10×10×15 mm.

Figure 9:
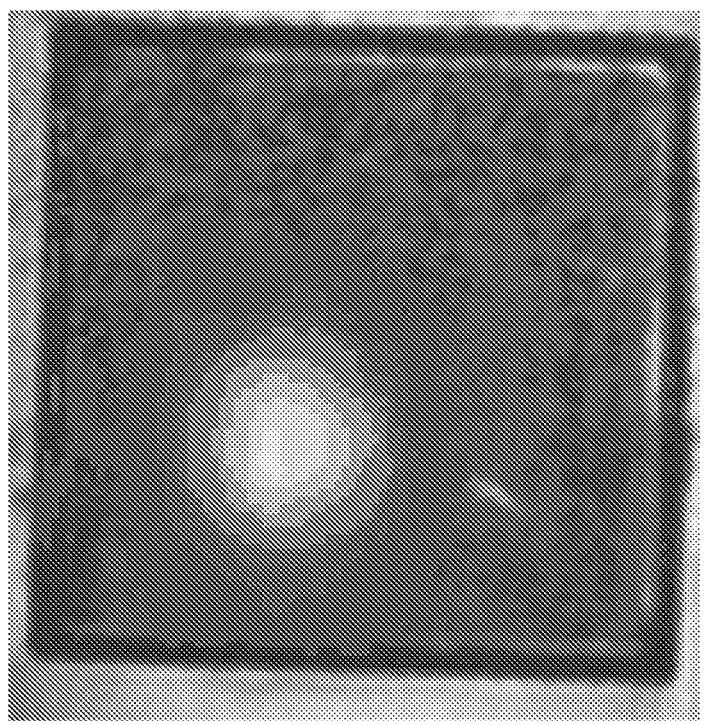
FIG. 9 is a real-time temperature map of ex vivo bovine liver tissue in the coronal plane.

FIG. 9 is a real time temperature map in the coronal image plane during a BH-sonication of the ex vivo bovine liver tissue described above. Temperature at the target location as well as in surrounding regions can be monitored in real time. This information can be utilized in closed-loop or user adjustable feedback control to avoid off-target temperature elevations and to perform safer treatments, as well as to control temperatures at the target. Different temperature limits and actions can be applied to different regions within the image using ROIs, action criteria, and logical conditions (e.g., AND, NAND, OR, NOR, XOR, etc.).

Figure 10:
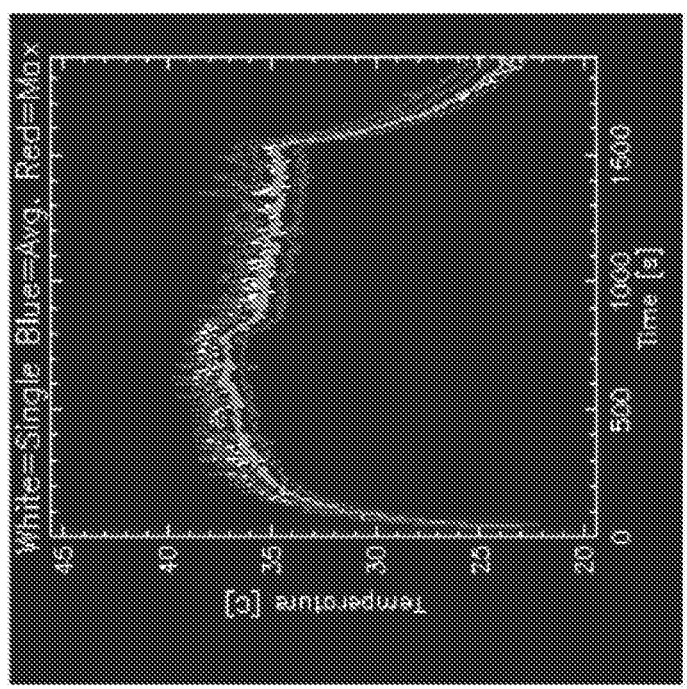
FIG. 10 is a graph depicting temperature over time for a region of the ex vivo bovine liver tissue.

FIG. 10 depicts temperatures at the target, calculated from the real time temperature maps during a BH-sonication within the ex vivo bovine liver. Curves show a maximum temperature, mean temperature in a 10×10 mm ROI centered on the target, and the standard deviations. Similar curves can be calculated from regions outside of the target. This information can be used in closed-loop or user-adjustable feedback control to change target location of an ultrasound beam or to adjust sonication parameters to regulate temperatures both within and outside of the target region. Different temperature limits and actions can be applied to different regions within the image using ROIs, action criteria, and logical conditions. In this example, sonication was switched to another location (layer) by an automatic feedback algorithm at 800 seconds when the mean temperature at the target reached 38° C.

FIG. 11A shows real time fast-field-echo (FFE) magnitude images during a BH-sonication within the ex vivo bovine liver in the coronal imaging plane. FIG. 11B shows the same information in the sagittal imaging plane. A transducer sonicates from left to right in the sagittal image. BH-lesion formation (indicated by arrows), corresponding to the planned locations and feedback ROIs, can be visualized in real time in these FFE images. This information can be utilized to control or limit off-target lesion formation to perform safer treatments, as well as to control the target region location, shape, size, and degree of homogenization or fractionation in real time. Different limits of signal intensity or elasticity change can be applied to different regions within the image using ROIs, action criteria, and logical conditions, based on baseline MRI signal intensity or elasticity measurements.

Figures 12A, 12B, 12C, 12D:
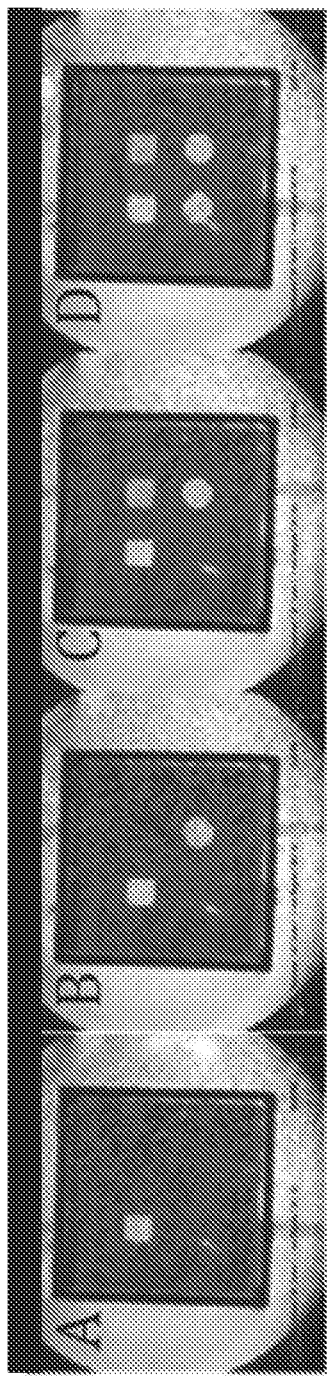
FIG. 12A is a real-time FFE image of the ex vivo bovine liver tissue showing one volumetric sonication.
FIG. 12B is a real-time FFE image of the ex vivo bovine liver tissue showing two volumetric sonications.
FIG. 12C is a real-time FFE image of the ex vivo bovine liver tissue showing three volumetric sonications.
FIG. 12D is a real-time FFE image of the ex vivo bovine liver tissue showing four volumetric sonications.

FIGS. 12A, 12B, 12C, and 12D are real time FFE magnitude images captured during a BH-sonication of the ex vivo bovine liver. The images represent the coronal imaging plane. BH-lesion formations, corresponding to the target locations and feedback ROIs, can be visualized in real time in these FFE images. FIG. 12A shows the ex vivo liver tissue after one volumetric BH sonication. FIG. 12B shows the liver tissue after two volumetric BH sonications. FIG. 12C shows the liver tissue after three volumetric BH sonications. FIG. 12D shows the liver tissue after four volumetric BH sonications. Unlike in ultrasound applications such as thermal ablation and mild hyperthermia that are purely thermal in nature, the BH lesions are clearly visible in real time MRI, and also persistent on MR images acquired post-sonication. This information is useful since feedback control can be performed not only based on the current target region that is being sonicated, but also on the previous targets and ROIs.

Figures 13A, 13B, 13C:
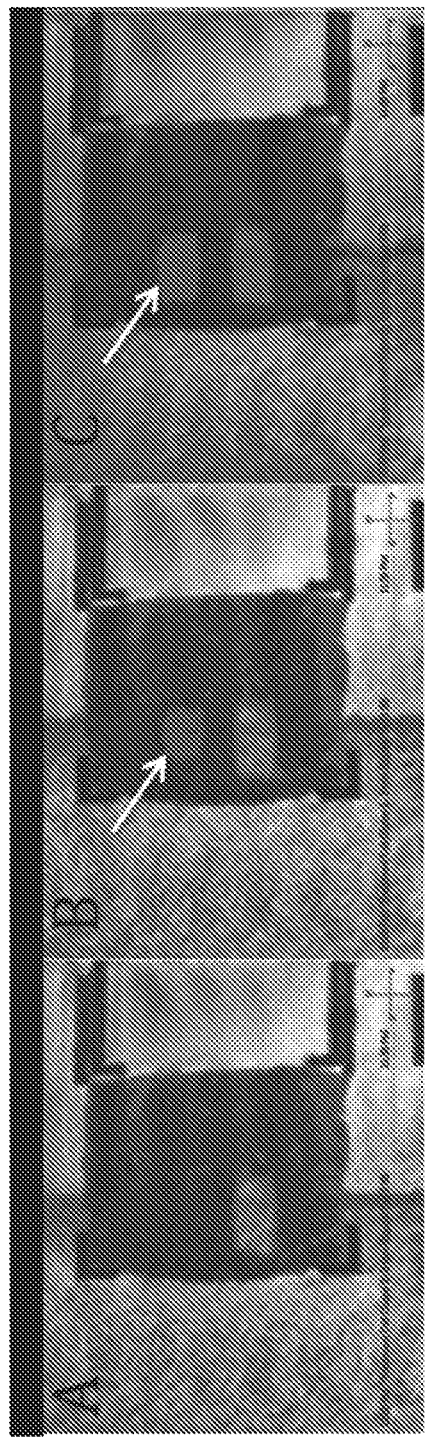
FIG. 13A is an FFE image of ex vivo bovine liver tissue after a first sonication.
FIG. 13B is an FFE image of the ex vivo bovine liver tissue during a second sonication.
FIG. 13C is an FFE image of the ex vivo bovine liver tissue after the second sonication.

FIGS. 13A, 13B, and 13C are real time FFE magnitude images during a BH-sonication of the ex vivo bovine liver in the sagittal imaging plane. BH-lesion formations, corresponding to the planned locations and feedback ROIs, can be visualized in real time in these FFE images. FIG. 13A shows the liver tissue after one volumetric BH sonication, but prior to starting a second volumetric BH sonication. FIG. 13B shows the liver tissue during a second volumetric BH sonication. FIG. 13C shows the liver tissue after completion of the second volumetric BH sonication. As shown in FIG. 13B, the mean signal intensity (indicated by an arrow) wasn't yet at a level corresponding to the action criteria, and thus the sonication was continued according to an automatic feedback algorithm. As shown in FIG. 13C, the sonication was stopped according to the feedback algorithm when the mean signal intensity within the ROI exceeded a threshold and thus the action criterion was fulfilled.

Figure 14:
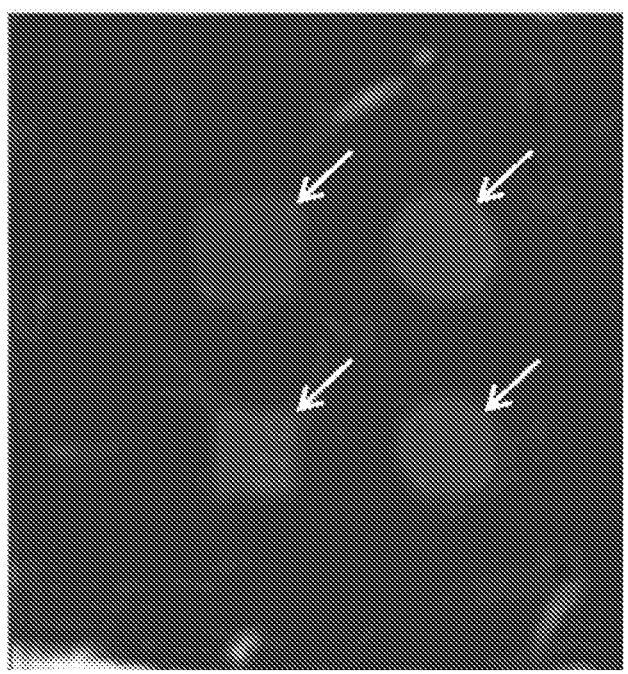
FIG. 14 is a T2-weighted image of the ex vivo bovine liver tissue after the completion of a sonication therapy.

FIG. 14 is a T2-weighted image captured after a BH-sonication of the ex vivo bovine liver tissue in the coronal imaging plane. BH-lesion locations, shapes, and sizes, corresponding to the planned locations and feedback ROIs, can be visualized and measured post-therapy, even without using MRI contrast agents. This information can be used to assess post-therapy outcomes and used in closed-loop or user-adjustable feedback control. For example, the information on lesion location, shape, size, and signal intensity when compared to neighboring tissue can be used to plan subsequent sonications aimed toward merging existing lesions into one contiguous lesion, re-treat a lesion, or to make a decision to treat other targets or to end treatment. Different MR-imaging methods may be needed to provide adequate contrast for specific tissue types.

While various example aspects and example embodiments have been disclosed herein, other aspects and embodiments will be apparent to those skilled in the art. The various example aspects and example embodiments disclosed herein are for purposes of illustration and are not intended to be limiting, with the true scope and spirit being indicated by the following claims.

The invention claimed is:

1. A method comprising:
displaying, via a user interface, an image representing first magnetic resonance imaging (MRI) data corresponding to biological tissue;
receiving, via the user interface, first input identifying two or more target regions of the biological tissue to be mechanically fractionated via exposure to first ultrasound waves and one or more avoidance regions of the biological tissue to be monitored;
applying the first ultrasound waves according to one or more first parameters to the two or more target regions, the one or more first parameters including a treatment trajectory, the applying the first ultrasound waves including applying the first ultrasound waves according to the treatment trajectory in which a focal point of the first ultrasound waves is directed sequentially upon each of the two or more target regions of the biological tissue, thereby mechanically fractionating at least a portion of the two or more target regions;
contemporaneous to or after applying the first ultrasound waves, acquiring second MRI data corresponding to the biological tissue, the second MRI data including a first portion corresponding to the two or more target regions and a second portion corresponding to the one or more avoidance regions;
determining, based on the second MRI data, one or more second parameters for applying second ultrasound waves to the two or more target regions of the biological tissue, the determining the one or more second parameters including determining, based on the second portion of the second MRI data, that a signal intensity of the one or more avoidance regions exceeds a threshold value, the one or more second parameters including a change to the treatment trajectory to redirect the second ultrasound waves; and
applying the second ultrasound waves to the biological tissue according to the one or more second parameters.

2. The method of claim 1, further comprising: prior to displaying the image, acquiring the first MRI data by using an MRI system.

3. The method of claim 1, further comprising:
receiving, via the user interface, second input that identifies the one or more second parameters,
wherein the one or more second parameters are determined additionally based on the received second input.

4. The method of claim 1, wherein the one or more first parameters include a first plurality of parameters, and the one or more second parameters include a second plurality of parameters, and more than one parameter of the second plurality of parameters is not equal to the corresponding parameters of the first plurality of parameters.

5. The method of claim 1, wherein the first and second MRI data include magnetic resonance elastography (MRE) data.

6. The method of claim 1, wherein the first and second MRI data include T2-weighted data.

7. A non-transitory computer readable medium storing instructions that, when executed by a device, cause the device to perform functions comprising:
displaying, via a user interface of the device, an image representing first magnetic resonance imaging (MRI) data corresponding to biological tissue;
receiving, via the user interface, first input identifying two or more target regions of the biological tissue to be mechanically fractionated via exposure to first ultrasound waves and one or more avoidance regions of the biological tissue to be monitored;
applying, via a transducer of the device, the first ultrasound waves to the two or more target regions according to one or more first parameters, the one or more first parameters including a treatment trajectory, the applying the first ultrasound waves including applying the first ultrasound waves according to the treatment trajectory in which a focal point of the first ultrasound waves is directed sequentially upon each of the two or more target regions of the biological tissue, thereby mechanically fractionating at least a portion of the two or more target regions;
contemporaneous to or after applying the first ultrasound waves, acquiring, via an MRI system of the device, second MRI data corresponding to the biological tissue, the second MRI data including a first portion corresponding to the two or more target regions and a second portion corresponding to the one or more avoidance regions;
determining, based on the second MRI data, one or more second parameters for applying second ultrasound waves to the two or more target regions of the biological tissue, the determining the one or more second parameters including determining, based on the second portion of the second MRI data, that a signal intensity of the one or more avoidance regions exceeds a threshold value, the one or more second parameters including a change to the treatment trajectory to redirect the second ultrasound waves; and
applying, via the transducer, the second ultrasound waves to the biological tissue according to the one or more second parameters.

8. The non-transitory computer readable medium of claim 7, the functions further comprising: prior to displaying the image, acquiring the first MRI data by using the MRI system.

9. The non-transitory computer readable medium of claim 7, wherein the one or more first parameters include a first plurality of parameters, and the one or more second parameters include a second plurality of parameters, and more than one parameter of the second plurality of parameters is not equal to the corresponding parameters of the first plurality of parameters.

10. The non-transitory computer readable medium of claim 7, wherein the first and second MRI data include magnetic resonance elastography (MRE) data.

11. The non-transitory computer readable medium of claim 7, wherein the first and second MRI data include T2-weighted data.

12. A device comprising:
one or more processors;
a user interface;
a transducer;
a magnetic resonance imaging (MRI) system; and
a non-transitory computer readable medium storing instructions that, when executed by the one or more processors, cause the device to perform functions comprising:
displaying, via the user interface, an image representing first MRI data corresponding to biological tissue;
receiving, via the user interface, first input identifying two or more target regions of the biological tissue to be mechanically fractionated via exposure to first ultrasound waves and one or more avoidance regions of the biological tissue to be monitored;
applying, via the transducer, the first ultrasound waves to the two or more target regions according to one or more first parameters, the one or more first parameters including a treatment trajectory, the applying the first ultrasound waves including applying the first ultrasound waves according to the treatment trajectory in which a focal point of the first ultrasound waves is directed sequentially upon each of the two or more target regions, thereby mechanically fractionating at least a portion of the two or more target regions;
contemporaneous to or after applying the first ultrasound waves, acquiring, via the MRI system, second MRI data corresponding to the biological tissue, the second MRI data including a first portion corresponding to the two or more target regions and a second portion corresponding to the one or more avoidance regions;
determining, based on the second MRI data, one or more second parameters for applying second ultrasound waves to the two or more target regions of the biological tissue, the determining the one or more second parameters including determining, based on the second portion of the second MRI data, that a signal intensity of the one or more avoidance regions exceeds a threshold value, the one or more second parameters including a change to the treatment trajectory to redirect the second ultrasound waves; and
applying, via the transducer, the second ultrasound waves to the biological tissue according to the one or more second parameters.

13. The device of claim 12, the functions further comprising: prior to displaying the image, acquiring the first MRI data by using the MRI system.

14. The device of claim 12, wherein the one or more first parameters include a first plurality of parameters, and the one or more second parameters include a second plurality of parameters, and more than one parameter of the second plurality of parameters is not equal to the corresponding parameters of the first plurality of parameters.

15. The device of claim 12, wherein the first and second MRI data include magnetic resonance elastography (MRE) data.

16. The device of claim 12, wherein the first and second MRI data include T2-weighted data.

* * * * *